(12) United States Patent
Melkent et al.

(10) Patent No.: US 10,933,172 B2
(45) Date of Patent: Mar. 2, 2021

(54) IMPLANTABLE MEDICAL DEVICES

(71) Applicant: Warsaw Orthopedic, Inc., Warsaw, IN (US)

(72) Inventors: Anthony J. Melkent, Memphis, TN (US); Brian R. Thoren, Memphis, TN (US); Timothy J. N. Smith, Kingston (CA); Ian D. Grant, Belleville (CA); Ian R. Dunkley, Kingston (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 84 days.

(21) Appl. No.: 15/088,798

(22) Filed: Apr. 1, 2016

(65) Prior Publication Data

US 2016/0213821 A1   Jul. 28, 2016

Related U.S. Application Data

(62) Division of application No. 12/508,856, filed on Jul. 24, 2009, now Pat. No. 9,399,086.

(51) Int. Cl.
*A61L 31/12* (2006.01)
*A61F 2/44* (2006.01)
(Continued)

(52) U.S. Cl.
CPC .......... *A61L 31/121* (2013.01); *A61F 2/4455* (2013.01); *A61L 27/425* (2013.01);
(Continued)

(58) Field of Classification Search
CPC ......... A61F 2310/00592; A61F 2/4455; A61L 27/58; A61L 27/56; A61L 31/121
See application file for complete search history.

(56) References Cited

U.S. PATENT DOCUMENTS

| 3,052,967 A | 9/1962 | Fischer |
| 3,090,094 A | 5/1963 | Schwartzwalker et al. |

(Continued)

FOREIGN PATENT DOCUMENTS

| EP | 0 335 359 A2 | 3/1989 |
| EP | 0 426 154 A3 | 10/1990 |

(Continued)

OTHER PUBLICATIONS

Milosevski et al., "Preparation and properties of dense and porous calcium phosphate", Ceramics International, 25;1999, pp. 693-696.*

*Primary Examiner* — Bruce E Snow
*Assistant Examiner* — Melissa A Hoban
(74) *Attorney, Agent, or Firm* — Sorell, Lenna & Schmidt, LLP

(57) ABSTRACT

Implantable medical devices are provided. In one embodiment, a device includes a body having an external surface defining an outer profile of the device. The body includes a porous matrix including a series of interconnected macropores defined by a plurality of interconnected struts each including a hollow interior. A filler material substantially fills at least a portion of the series of interconnected macropores. The external surface of the body includes a plurality of openings communicating with the hollow interior of at least a portion of the plurality of interconnected struts. In a further aspect of this embodiment, the external surface includes exposed areas of the filler material and porous matrix in addition to the exposed openings. In another aspect, the porous matrix is formed from a bioresorbable ceramic and the filler material is a biologically stable polymeric material. Still, other aspects related to this and other embodiments are also disclosed.

10 Claims, 3 Drawing Sheets

(51) Int. Cl.
| | | |
|---|---|---|
| *A61L 27/42* | (2006.01) | |
| *A61L 27/58* | (2006.01) | |
| *C08L 71/12* | (2006.01) | |
| *A61L 27/56* | (2006.01) | |
| *B05D 1/18* | (2006.01) | |
| *B05D 3/02* | (2006.01) | |
| *B29C 45/00* | (2006.01) | |
| *B29C 45/14* | (2006.01) | |
| *C04B 38/00* | (2006.01) | |
| *C04B 41/45* | (2006.01) | |
| *C04B 41/81* | (2006.01) | |
| *A61F 2/30* | (2006.01) | |
| *A61L 27/46* | (2006.01) | |
| *B29K 71/00* | (2006.01) | |
| *B29L 31/00* | (2006.01) | |

(52) U.S. Cl.
CPC ............... *A61L 27/56* (2013.01); *A61L 27/58* (2013.01); *B05D 1/18* (2013.01); *B05D 3/0272* (2013.01); *B29C 45/0055* (2013.01); *B29C 45/14795* (2013.01); *C04B 38/0051* (2013.01); *C04B 41/4586* (2013.01); *C04B 41/81* (2013.01); *C08L 71/12* (2013.01); *A61F 2/30724* (2013.01); *A61F 2002/30028* (2013.01); *A61F 2002/30032* (2013.01); *A61F 2002/30062* (2013.01); *A61F 2002/30187* (2013.01); *A61F 2002/30593* (2013.01); *A61F 2002/30957* (2013.01); *A61F 2002/30973* (2013.01); *A61L 27/46* (2013.01); *A61L 2400/08* (2013.01); *A61L 2400/18* (2013.01); *A61L 2420/02* (2013.01); *A61L 2420/04* (2013.01); *B29C 2045/0058* (2013.01); *B29K 2071/00* (2013.01); *B29L 2031/7532* (2013.01); *C04B 2235/606* (2013.01)

(56) References Cited

U.S. PATENT DOCUMENTS

| | | | |
|---|---|---|---|
| 3,111,396 A | 11/1963 | Ball | |
| 3,362,818 A | 1/1968 | Schwarzkopf et al. | |
| 3,408,180 A | 10/1968 | Winkler | |
| 3,470,117 A | 9/1969 | Pearce | |
| 3,893,917 A | 7/1975 | Pryor et al. | |
| 3,899,556 A | 8/1975 | Heide et al. | |
| 3,929,971 A | 12/1975 | Roy | |
| 3,939,002 A | 2/1976 | Washbourne | |
| 3,946,039 A | 3/1976 | Walz | |
| 3,947,363 A | 3/1976 | Pryor et al. | |
| 3,962,081 A | 6/1976 | Yarwood et al. | |
| 4,123,285 A | 10/1978 | Schuster et al. | |
| 4,149,894 A | 4/1979 | Ebihara et al. | |
| 4,156,943 A | 6/1979 | Collier | |
| 4,222,128 A | 9/1980 | Tomonaga et al. | |
| 4,371,484 A | 2/1983 | Inukai et al. | |
| 4,448,758 A | 5/1984 | Nagai et al. | |
| 4,517,069 A | 5/1985 | Hamey et al. | |
| 4,600,546 A | 7/1986 | Grundei | |
| 4,608,350 A | 8/1986 | Howard, Jr. | |
| 4,610,692 A | 9/1986 | Eitenmuller et al. | |
| 4,629,464 A | 12/1986 | Takata et al. | |
| 4,654,314 A | 3/1987 | Takagi et al. | |
| 4,656,196 A | 4/1987 | Kelly et al. | |
| 4,670,477 A | 6/1987 | Kelly et al. | |
| 4,728,570 A | 3/1988 | Ashman et al. | |
| 4,737,411 A | 4/1988 | Graves et al. | |
| 4,843,112 A | 6/1989 | Gerhart et al. | |
| 4,849,285 A | 7/1989 | Dillon | |
| 4,887,795 A | 12/1989 | Nemeth et al. | |
| 4,892,786 A | 1/1990 | Newkirk | |
| 4,897,370 A | 1/1990 | Horiguchi et al. | |
| 4,900,698 A | 2/1990 | Lundsager | |
| 4,919,751 A | 4/1990 | Sumita et al. | |
| 4,969,913 A | 11/1990 | Ojima | |
| 4,975,230 A | 12/1990 | Pinkhasov | |
| 4,976,736 A * | 12/1990 | White et al. | ................ 424/423 |
| 5,007,929 A | 4/1991 | Quaid | |
| 5,030,396 A | 7/1991 | Saita et al. | |
| 5,084,051 A | 1/1992 | Tormala et al. | |
| 5,093,289 A | 3/1992 | Braetsch et al. | |
| 5,133,755 A | 7/1992 | Brekke | |
| 5,141,510 A | 8/1992 | Takagi et al. | |
| 5,171,720 A | 12/1992 | Kawakami | |
| 5,262,203 A | 11/1993 | Lesher et al. | |
| 5,338,772 A | 8/1994 | Bauer et al. | |
| 5,384,171 A * | 1/1995 | Prucher | ................ C04B 35/71 |
| | | | 428/304.4 |
| 5,433,751 A | 7/1995 | Christel et al. | |
| 5,464,440 A | 11/1995 | Johansson | |
| 5,591,453 A | 1/1997 | Ducheyne et al. | |
| 5,626,861 A | 5/1997 | Laurencin et al. | |
| 5,676,745 A | 10/1997 | Kelly et al. | |
| 5,766,618 A | 6/1998 | Laurencin et al. | |
| 5,872,159 A | 2/1999 | Cougoulic | |
| 5,876,446 A | 3/1999 | Agrawal et al. | |
| 5,977,204 A | 11/1999 | Boyan et al. | |
| 5,981,619 A | 11/1999 | Shikinami et al. | |
| 5,989,289 A * | 11/1999 | Coates et al. | ................ 623/17.16 |
| 6,102,948 A | 8/2000 | Brosnahan, III | |
| 6,110,484 A | 8/2000 | Sierra | |
| 6,111,172 A | 9/2000 | Ripamonti et al. | |
| 6,126,688 A | 10/2000 | McDonnell | |
| 6,129,757 A | 10/2000 | Weadock | |
| 6,136,029 A | 10/2000 | Johnson et al. | |
| 6,261,322 B1 | 7/2001 | Despres et al. | |
| 6,302,913 B1 | 10/2001 | Ripamonti et al. | |
| 6,306,169 B1 | 10/2001 | Lee et al. | |
| 6,323,146 B1 | 11/2001 | Pugh et al. | |
| 6,337,198 B1 | 1/2002 | Levene et al. | |
| 6,344,496 B1 | 2/2002 | Niederauer et al. | |
| 6,376,573 B1 | 4/2002 | White et al. | |
| 6,454,811 B1 | 9/2002 | Sherwood et al. | |
| 6,458,159 B1 | 10/2002 | Thalgott | |
| 6,458,162 B1 | 10/2002 | Koblish et al. | |
| 6,479,418 B2 * | 11/2002 | Li | ................ A61L 27/12 |
| | | | 106/35 |
| 6,485,521 B1 | 11/2002 | Say et al. | |
| 6,503,279 B1 | 1/2003 | Webb et al. | |
| 6,511,510 B1 | 1/2003 | de Bruijn et al. | |
| 6,544,290 B1 | 4/2003 | Lee et al. | |
| 6,569,201 B2 | 5/2003 | Moumene et al. | |
| 6,583,232 B1 | 6/2003 | Brown | |
| 6,599,323 B2 | 7/2003 | Melican et al. | |
| 6,599,517 B1 | 7/2003 | Ljusberg-Wahren et al. | |
| 6,602,293 B1 | 8/2003 | Biermann et al. | |
| 6,605,293 B1 | 8/2003 | Giordano et al. | |
| 6,790,233 B2 | 9/2004 | Brodke et al. | |
| 6,843,805 B2 | 1/2005 | Webb et al. | |
| 6,846,327 B2 | 1/2005 | Khandkar et al. | |
| 6,858,041 B2 | 2/2005 | Richter et al. | |
| 6,921,410 B2 | 7/2005 | Porter | |
| 7,001,385 B2 | 2/2006 | Bonutti | |
| 7,052,710 B2 | 5/2006 | Giordano et al. | |
| 7,066,962 B2 | 6/2006 | Swords | |
| 7,105,030 B2 | 9/2006 | Despres, III et al. | |
| 7,119,038 B2 | 10/2006 | Lin et al. | |
| 7,122,057 B2 | 10/2006 | Beam et al. | |
| 7,163,651 B2 | 1/2007 | Chern Lin et al. | |
| 7,230,039 B2 | 6/2007 | Trieu et al. | |
| 8,114,336 B2 * | 2/2012 | Yang | ................ A61L 27/10 |
| | | | 264/344 |
| 8,851,891 B2 * | 10/2014 | Lomicka | ................ A61C 8/0033 |
| | | | 433/173 |
| 2002/0143403 A1 | 10/2002 | Vaidyanathan et al. | |
| 2003/0003160 A1 * | 1/2003 | Pugh et al. | ................ 424/602 |
| 2003/0003127 A1 | 2/2003 | Brown et al. | |
| 2003/0031698 A1 | 2/2003 | Roeder et al. | |
| 2003/0050707 A1 | 3/2003 | Landingham | |
| 2003/0065393 A1 | 4/2003 | Moumene et al. | |
| 2003/0072790 A1 | 4/2003 | Tsai et al. | |

(56) References Cited

U.S. PATENT DOCUMENTS

| | | | |
|---|---|---|---|
| 2003/0100946 A1 | 5/2003 | Richter et al. | |
| 2003/0114932 A1 | 6/2003 | Webb et al. | |
| 2003/0114936 A1 | 6/2003 | Sherwood et al. | |
| 2003/0175321 A1* | 9/2003 | Sapieszko et al. | 424/423 |
| 2004/0002770 A1 | 1/2004 | King et al. | |
| 2004/0024081 A1 | 2/2004 | Trieu et al. | |
| 2004/0024470 A1* | 2/2004 | Giordano et al. | 623/23.51 |
| 2004/0093089 A1 | 5/2004 | Ralph et al. | |
| 2004/0265385 A1* | 12/2004 | West | 424/484 |
| 2005/0042253 A1 | 2/2005 | Farrar et al. | |
| 2005/0100578 A1* | 5/2005 | Schmid | A61F 2/28 424/423 |
| 2005/0113934 A1* | 5/2005 | Kim | A61F 2/30767 623/23.56 |
| 2005/0158535 A1* | 7/2005 | Zhang | A61L 27/46 428/304.4 |
| 2005/0171615 A1 | 8/2005 | Georgette et al. | |
| 2005/0246021 A1 | 11/2005 | Ringeisen et al. | |
| 2006/0121084 A1* | 6/2006 | Borden | A61B 17/866 424/426 |
| 2006/0198939 A1 | 9/2006 | Smith et al. | |
| 2006/0199876 A1 | 9/2006 | Troczynski et al. | |
| 2006/0276788 A1 | 12/2006 | Berry et al. | |
| 2006/0276875 A1 | 12/2006 | Stinson et al. | |
| 2007/0003753 A1 | 1/2007 | Asgari | |
| 2007/0015110 A1 | 1/2007 | Zhang | |
| 2007/0129810 A1 | 6/2007 | Farrar et al. | |
| 2007/0260324 A1 | 11/2007 | Joshi et al. | |
| 2007/0270844 A1 | 11/2007 | Lin et al. | |
| 2007/0278720 A1 | 12/2007 | Wang et al. | |
| 2007/0282434 A1 | 12/2007 | Wang et al. | |
| 2008/0188938 A1 | 8/2008 | Gazza | |
| 2008/0206297 A1 | 8/2008 | Roeder et al. | |
| 2008/0249637 A1 | 10/2008 | Asgari | |
| 2008/0306554 A1 | 12/2008 | McKinley | |
| 2009/0093888 A1 | 4/2009 | Dawson et al. | |
| 2009/0112315 A1 | 4/2009 | Zimmer | |
| 2009/0305017 A1* | 12/2009 | His | B01D 39/2093 428/220 |
| 2010/0003904 A1* | 1/2010 | Duescher | B24B 37/14 451/259 |
| 2010/0021518 A1* | 1/2010 | Scifert | A61K 9/0024 424/423 |
| 2010/0022479 A1* | 1/2010 | Bourban | A61F 2/28 514/102 |
| 2011/0313538 A1* | 12/2011 | Oh | A61L 27/56 623/23.61 |
| 2012/0034440 A1* | 2/2012 | Schmidt | 428/217 |
| 2013/0330394 A1* | 12/2013 | Ponticiello | A61L 27/46 424/426 |

FOREIGN PATENT DOCUMENTS

| | | |
|---|---|---|
| EP | 0 560 279 A1 | 3/1993 |
| WO | WO 97/46178 | 12/1997 |
| WO | WO 01/54746 A2 | 8/2001 |
| WO | WO 2004/024201 A2 | 3/2004 |
| WO | WO 2007/051307 A2 | 5/2007 |

* cited by examiner

US 10,933,172 B2

IMPLANTABLE MEDICAL DEVICES

This application is a divisional application of U.S. patent application Ser. No. 12/508,856, filed Jul. 24, 2009, which is incorporated by reference herein, in its entirety.

BACKGROUND

The present invention relates to implantable medical devices and methods for making and using such devices, and more particularly, but not exclusively, relates to devices for promoting bone and/or tissue ingrowth, supporting the natural bone remodeling process through osteoclast and osteoblast activity, and/or for stabilizing and promoting bone and/or tissue fusion between adjacent bones or bony tissues.

Various types of devices, implants and systems have been used to stabilize and promote bone and tissue fusion between adjacent bones or bony tissues in a patient. In one form, implants or devices formed of autograft (bone removed from the patient) or allograft (bone taken from another person) have been used because of their osteoinductive and/or osteoconductive properties. However, various difficulties have been encountered with the use of autograft and allograft. For example, autograft presents high incidences of donor site morbidity, the necessity of a painful second 'harvesting' surgical procedure, and the absence of large quantities of bone available for grafting, while allograft presents concerns related to disease transmission, difficulty of procurement and processing, uncertain immune response, and premature resorption. In addition, various considerations related to the anatomical space in which the implant or device is implanted, such as compressive loads for example, can present difficulties in implementing autograft or allograft and/or cause undesirable side effects if autograft or allograft is utilized.

While developments in the stabilization and fusion of adjacent bones or bony tissues have provided steps in the right direction, there remains a need for further development in this area of technology.

SUMMARY

One non-limiting embodiment of the present application is directed to an implantable medical device. In one aspect of this embodiment, the device is configured for promoting bone and/or tissue ingrowth, supporting the natural bone remodeling process through osteoclast and osteoblast activity, or for stabilizing and promoting bone and/or tissue fusion between adjacent bones or bony tissues, although devices configured for providing a combination of some or all of the foregoing features are disclosed.

In another embodiment, an implantable medical device includes a body including an external surface defining an outer profile of the device. The body also includes a porous matrix including a series of interconnected macropores defined by a plurality of interconnected struts each including a hollow interior. A filler material substantially fills at least a portion of the series of interconnected macropores. A plurality of openings extend through at least a portion of the external surface and communicate with the hollow interior of at least a portion of the plurality of interconnected struts. In a further aspect of this embodiment, the external surface is defined by the plurality of openings, exposed areas of the porous matrix, and exposed areas of the filler material. In another aspect of this embodiment, the porous matrix is formed of a ceramic material and the filler material is a polymeric material. In yet a further aspect, the ceramic material is bioresorbable and the polymeric material is biologically stable. In still another aspect, the filler material is infused throughout and substantially fills each one of the series of interconnected macropores.

In still another embodiment, a method includes providing an implantable medical device that includes a body including an external surface defining an outer profile of the device. The body also includes a porous matrix including a series of interconnected macropores defined by a plurality of interconnected struts each including a hollow interior; a filler material substantially filling at least a portion of the series of interconnected macropores; and a plurality of openings extending through at least a portion of the external surface and communicating with the hollow interior of at least a portion of the plurality of interconnected struts. The method further includes positioning the device between adjacent bony portions. In a further aspect of this embodiment, positioning the device between adjacent bony portions includes inserting the device into a disc space between adjacent vertebral bodies.

In yet another embodiment, an implantable medical device includes a body including an external surface defining an outer profile of the device. The body also includes a bioresorbable ceramic matrix including a series of interconnected macropores defined by a plurality of interconnected struts that further define a plurality of interconnected passages isolated from the series of interconnected macropores. A biologically stable polymeric material is infused throughout and substantially fills the series of interconnected macropores, while the plurality of interconnected passages are substantially free of the polymeric material. In one aspect of this embodiment, at least a portion of the plurality of interconnected passages extends through and opens at the external surface of the body. In another aspect of this embodiment, the body is configured to be positioned between adjacent bones or bony tissue, and the external surface includes oppositely positioned bone engaging portions each including a plurality of bone engaging projections structured to engage with the adjacent bones or bony tissue.

In another embodiment, a method for producing a medical implant includes providing a bioresorbable ceramic matrix including a series of interconnected macropores defined by a plurality of interconnected struts, the interconnected struts including a plurality of interconnected internal passages positioned therein; impregnating the ceramic matrix with a biologically stable polymeric material to provide a composite blank; and processing the composite blank to provide an implant body including an external surface defining an outer profile of a desired configuration and shape for implantation, the processing including exposing at least a portion of the interconnected internal passages at the external surface. In a further aspect of this embodiment, the external surface further includes one or more exposed areas of the polymeric material and one or more exposed areas of the ceramic matrix.

In yet another embodiment, an implantable medical device includes a body having an external surface defining an outer profile of the device. The external surface includes one or more exposed areas of a matrix that includes one or more openings and a biologically stable filler material substantially filling at least a portion of the one or more openings. Following implantation, the matrix undergoes a remodeling process in which osteoclast activity progressively removes portions of the matrix and osteoblast activity progressively replaces the removed portions of the matrix with new bone tissue. Initiation of the remodeling process is generally limited to the one or more exposed areas of the matrix. In one aspect of this embodiment, the initiation of the remodeling process is limited to those areas of the matrix that are exposed at or before implantation of the device. In another aspect of this embodiment, the remodeling process progressively replaces the matrix beginning at the external surface and moving progressively inwardly to the interior of the device until all or substantially all of the matrix has been replaced by new bone tissue. In yet another aspect, the matrix is formed by Skelite® and the biologically stable filler material is selected from polyetheretherketone (PEEK), carbon-reinforced PEEK, and polyetherketoneketone (PEKK).

Another embodiment of the present application is directed to a unique device for stabilization of adjacent bones or bony tissues. Other embodiments include unique methods, systems, devices, equipment and/or apparatuses directed to the promotion of bone and/or tissue ingrowth, promotion of the natural bone remodeling process by supporting osteoclast and osteoblast activity, and/or the stabilization and fusion of adjacent bones or bony tissues. In still other embodiments, different forms and applications of the present invention are envisioned.

Further embodiments, forms, features, aspects, benefits, objects and advantages of the present invention shall become apparent from the detailed description and figures provided herewith.

DESCRIPTION OF THE ILLUSTRATED EMBODIMENTS

Figure 1:
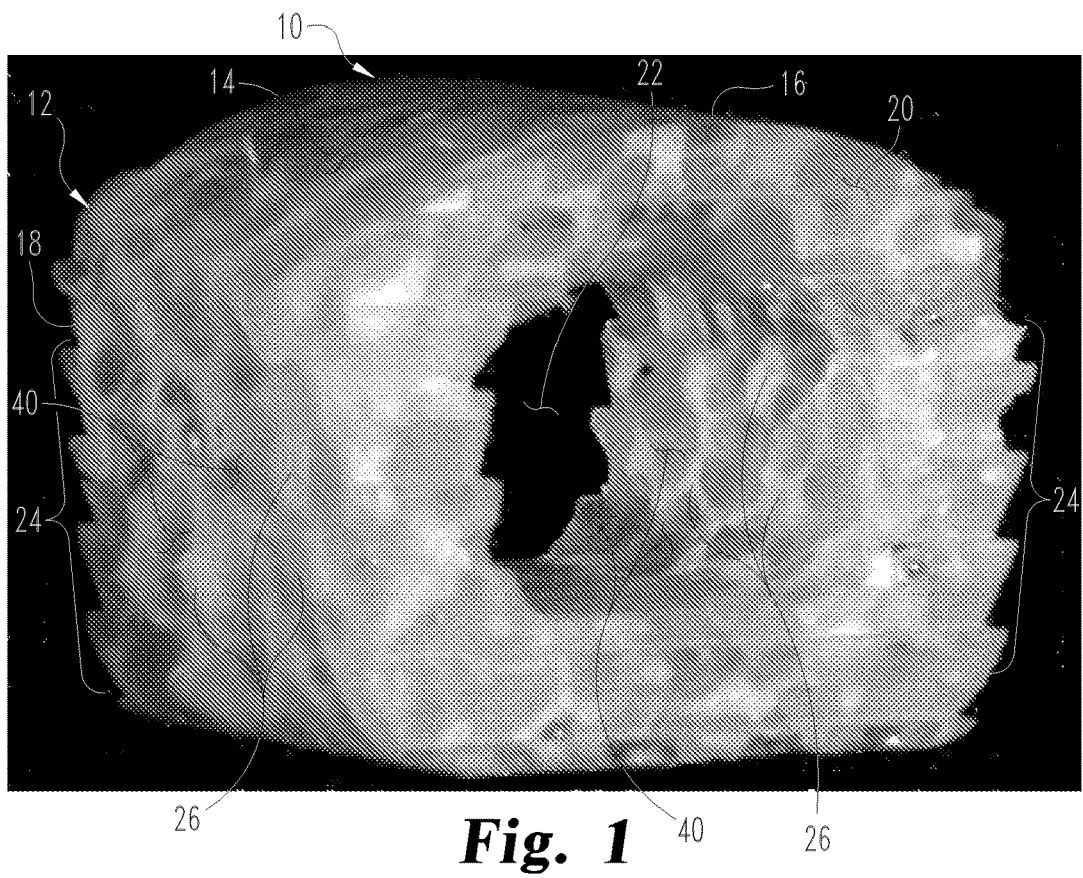
FIG. 1 depicts a photographic image of one embodiment implantable medical device.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices and described methods, and any such further applications of the principles of the invention as illustrated herein are contemplated as would normally occur to one skilled in the art to which the invention relates.

Implantable medical devices, implants and methods for making and using such devices and implants are provided. More particularly, in one embodiment, a device is provided that promotes bone and/or tissue ingrowth, promotes the natural bone remodeling process by supporting osteoclast and osteoblast activity, stabilizes adjacent bones or bony tissues, and/or promotes bone or tissue fusion between the adjacent bones or bony tissues, although devices configured for providing a combination of some or all of the foregoing features are disclosed. In one particular aspect of this embodiment, the device includes mechanical properties that emulate bone and are suitable for sustaining compressive loads at a selected anatomical site, such as a location between the adjacent bones or bony tissue. Generally, the device of this embodiment includes a porous matrix formed of an osteoconductive and/or osteoinductive material, such as a calcium-based ceramic which may be resorbable over time following implantation. In one particular form, the matrix is formed of a ceramic material that undergoes a remodeling process having aspects that are substantially similar to certain aspects of the natural bone remodeling process. More particularly, in this form the ceramic material is progressively removed by osteoclast activity, with the removed portion of the ceramic material being progressively replaced by new bone formed through osteoblast activity. Further details regarding this feature will be provided below. The porous matrix also includes a series of interconnected macropores defined by a plurality of interconnected struts, with each of the struts including a hollow interior, further details of which will be provided below. At least a portion of the interconnected series of macropores are substantially filled by a filler material, although in other forms each one of the interconnected series of macropores is infused with and substantially filled by the filler material, while the hollow interiors of the interconnected struts remain substantially open or free of the filler material. In one form, the filler material may be biologically stable, such as a biostable polymeric material. As used herein, the term "biologically stable" is used to refer to materials that remain substantially intact or unresorbed at, and following, implantation into a biological setting. However, in another form, it is contemplated that the filler material may be bioresorbable and become resorbed at the same time as the porous matrix is resorbed or after the porous matrix has become resorbed. In one form, the device also includes an external surface having a plurality of openings extending therethrough and communicating with the hollow interior(s) of at least a portion of the plurality of struts.

In this manner, all or part of the external surface of the device is arranged to include one or more exposed areas of the porous matrix formed of the osteoconductive and/or osteoinductive material and one or more exposed areas of the filler material in addition to the exposed openings in communication with the hollow interiors of at least a portion of the struts. Among other features, this arrangement provides an external surface that can promote bone attachment and bonding at the exposed area(s) of the porous matrix, as well as bone and/or tissue ingrowth and penetration into the device through the openings communicating with the hollow interiors of at least a portion of the interconnected struts. These features may, inter alia, facilitate enhanced interlocking of the device between the adjacent bones or bony tissue, promote fusion between the adjacent bones or bony tissues, and/or decrease the time required to achieve fusion between the adjacent bones or bony tissues. Moreover, the openings in communication with the hollow interiors of at least a portion of the interconnected struts will generally allow tissue infusion into the device more quickly, thereby providing anchoring of the device earlier in the healing period following implantation. In a further aspect where the osteoconductive and/or osteoinductive material is resorbable over time following implantation, the progressive integration of the device due to the resorbable nature of the porous matrix increases the level of anchoring and interlocking of the device that is achieved by the early bone and/or tissue infusion into the hollow interiors of the struts.

Moreover, in the form where the porous matrix is formed of a ceramic material that undergoes a remodeling process having aspects that are substantially similar to certain aspects of the natural bone remodeling process, the device includes surface chemistry that promotes osteoclast activity that allows bone bonding and formation at the exposed area(s) of the porous matrix and along the interior surfaces of the hollow interiors of the struts. More particularly, osteoclast activity may progressively remove portions of the porous matrix exposed at the external surface of the device as well as along the interior surfaces of the hollow struts. Osteoblast activity then correspondingly and progressively replaces the removed portions of the porous matrix with new bone tissues. Similarly, the hollow interiors of the interconnected struts provide additional material exposure at which osteoclast and corresponding osteoblast activity may occur to progressively replace the material of the porous matrix with new bone tissue. Likewise, the interlocking of the device between the adjacent bones or bony tissues is enhanced and the tissue ingrowth in the hollow interiors expands as the material of the porous matrix is remodeled.

In addition to the foregoing, it should be appreciated that the filler material provides a stable surface upon which the adjacent bones or bony tissues can be supported. The filler material also provides the device with high fracture toughness and a modulus of elasticity similar to bone while reinforcing the porous matrix so the device can withstand loads and stresses commonly encountered at various skeletal locations. Moreover, when the osteoconductive and/or osteoinductive material is resorbable over time following implantation and the filler material is biologically stable, it can continue to provide support to the adjacent bones or bony tissue following the resorption of the porous matrix. Indeed, in this form, the biologically stable filler material generally becomes a porous matrix into and through which bone and/or tissue infuse contemporaneously with or following the resorption of the porous matrix. Further details regarding these and other details of the devices disclosed and described in this document will be provided below.

In an alternative embodiment, a device is provided that includes a body formed by a ceramic matrix that includes one or more openings and a biologically stable filler material that substantially fills at least a portion of the openings, although in one or more forms it is contemplated that the biologically stable filler material may be infused throughout and substantially fill all of the openings. In one form of this embodiment, the openings are defined by a series of interconnected macropores. In another form however, the openings are defined by channels or passages that extend partially into or through the body. Still, in another form the ceramic body includes an engineered or structured geometry in the form of a framework that defines the openings. In one form of this embodiment, the device includes an external surface that defines an outer profile of the device and includes one or more exposed areas of the ceramic matrix and filler material, although it should be appreciated that the entirety of the external surface could be defined by exposed areas of the ceramic matrix and filler material. The ceramic matrix is formed of a ceramic material that undergoes a remodeling process having aspects that are substantially similar to certain aspects of the natural bone remodeling process. More particularly, in this form the ceramic material is progressively removed by osteoclast activity, with the removed portions of the ceramic material being progressively replaced by new bone formed through osteoblast activity. Similarly, following implantation of the device the ceramic matrix undergoes a remodeling process in which osteoclast activity progressively removes portions of the ceramic matrix and osteoblast activity progressively replaces the removed portions of the ceramic matrix with new bone tissue. In one aspect of this embodiment, initiation of the remodeling process is limited to the areas of the ceramic matrix that are exposed on the external surface of the device. More particularly, it should be appreciated that the ceramic matrix will be remodeled into new bone tissue by a process that begins at the external surface of the device and progressively continues over time toward or into the interior of the device. Likewise, since the filler material in this embodiment is biologically stable, the progress of the remodeling process toward or into the interior of the device can only originate at or from the exposed areas of the ceramic matrix on the external surface of the device. In another more particular aspect, initiation of the remodeling process may be limited to the areas of the ceramic matrix that are exposed on the external surface of the device at or before implantation.

While not previously discussed, the ceramic matrix of this embodiment also includes a plurality of interconnected struts that define the openings. In contrast to the embodiment described above, in this embodiment it is contemplated that each of the struts may be provided with a solid or filled cross section, although forms where each of the struts is provided with hollow interiors are also contemplated. Similarly, dependent on the form of the ceramic matrix, it is contemplated that in one or more forms the external surface of the device of this embodiment can be provided with openings extending therethrough and communicating with the hollow interior(s) of at least a portion of the plurality of struts.

Similar to the embodiment discussed above, the device of this embodiment may promote bone and/or tissue ingrowth, promote the natural bone remodeling process by supporting osteoclast and osteoblast activity, stabilize adjacent bones or bony tissues, and/or promote bone and/or tissue fusion between the adjacent bones or bony tissues. In one particular aspect of this embodiment, the device includes mechanical properties that emulate bone and are suitable for sustaining compressive loads at a selected anatomical site, such as a location between the adjacent bones or bony tissue. In addition, the external surface of the device of this embodiment includes surface chemistry that allows bone bonding and formation to begin at the exposed area(s) of the ceramic matrix and progressively continue from the exposed areas toward or into the internal portions of the device. Likewise, the interlocking of the device between the adjacent bones or bony tissues is enhanced and the tissue ingrowth into the device expands the ceramic matrix is remodeled.

Furthermore, the biologically stable material of this form provides a stable surface upon which the adjacent bones or bony tissues can be supported. The filler material also provides the device with high fracture toughness and a modulus of elasticity similar to bone while reinforcing the ceramic matrix so the device can withstand loads and stresses commonly encountered at various skeletal locations. Moreover, as the ceramic matrix is progressively remodeled and replaced by new bone, the filler material can continue to provide support to the adjacent bones or bony tissues. Further details regarding these and other details of the devices disclosed and described in this document will be provided below.

It is contemplated that the devices described above may be used at any skeletal location in any of a wide variety of applications where bone or tissue repair or growth is necessary or desired. In one more particular yet non-limiting form, the device may be configured for positioning between adjacent bones or bony tissues to provide support along a load bearing axis of the bones or bony tissues, although non-load bearing applications are also contemplated. For example, referring now to FIG. 1, a photographic image depicts an end view of an interbody implant device 10 structured to facilitate fusion between adjacent vertebral bodies. Device 10 generally includes a "D-shaped" body 12 structured for positioning in the disc space between adjacent vertebral bodies. Body 12 also has an external surface 14 extending around the outer profile and following the shape of device 10. Device 10 also includes a sidewall 16 extending around and enclosing a hollow chamber 22 into which bone growth enhancing materials, such as bone chips, bone morphogenetic protein, LIM mineralization proteins (LMPs) and other growth factors, may be positioned. External surface 14 includes oppositely positioned top and bottom portions 18, 20 that are formed with projections 24 structured to engage with the adjacent vertebral bodies and resist expulsion of device 10 from the disc space. In one or more forms, top and bottom portions 18, 20 may be angled relative to one another to provide a configuration that corresponds to the lordotic angle between the adjacent vertebral bodies between which device 10 will be positioned. Moreover, while not illustrated, it should be appreciated that device 10 may be provided with one or more tool engagement portions to facilitate engagement and placement of the device in the disc space with a suitable instrument. It is also contemplated that device 10 could be provided with alternative external configurations, non-limiting examples of which are disclosed in U.S. Pat. Nos. 7,192,446, 6,595,995, 6,613,091, 6,645,206, 6,695,851, 6,174,311, 6,610,065, 6,610,089, 6,096,038, 6,746,484, 6,471,724, 6,764,491, 6,830,570, 6,447,547, 6,991,654, 5,797,909, 5,669,909, 5,782,919, 5,984,967, 6,206,922, 6,245,072, and 6,375,655 and in U.S. Patent Publication No. 2008/0161927.

Figure 5:
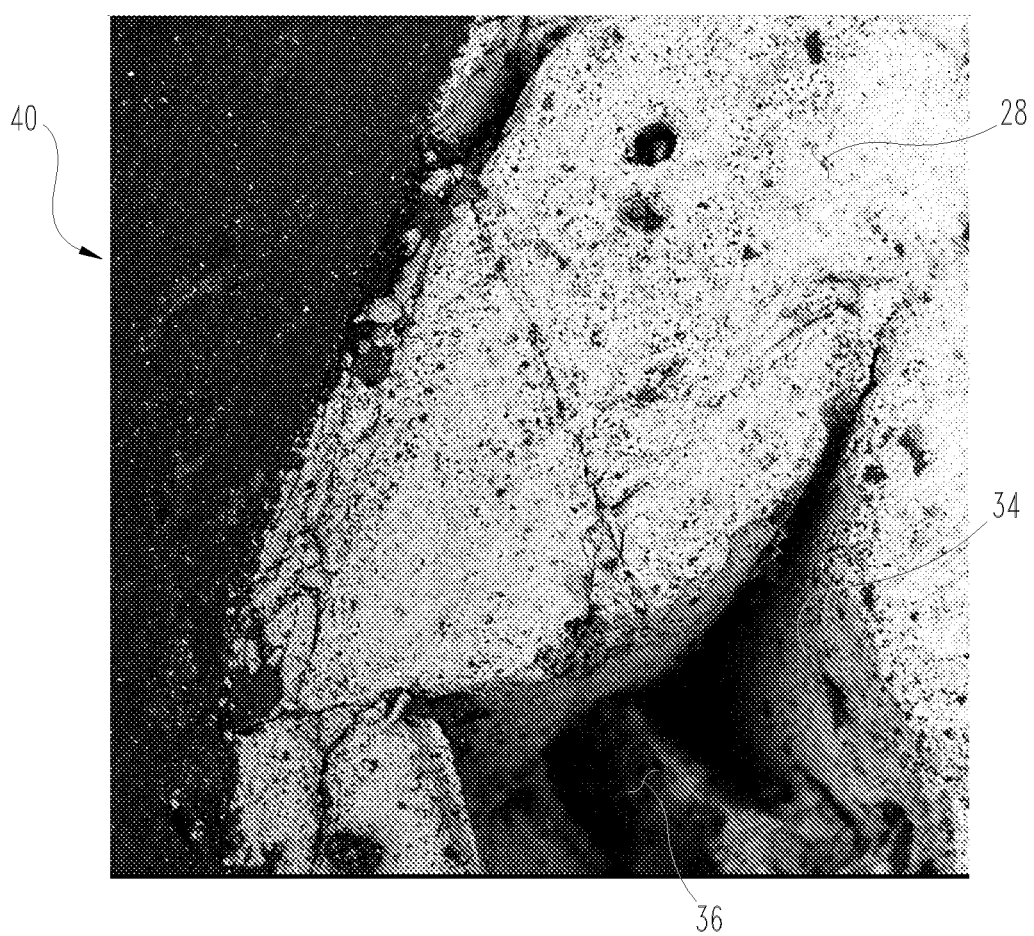
FIG. 5 depicts a magnified photographic image representative of the external surface of the implantable medical device of FIG. 1.

As also illustrated in FIG. 1, device 10 includes a matrix 26 and a filler material 40 which has been infused into and throughout openings of the matrix 26. More particularly, in the illustrated form, filler material 40 is infused into and throughout openings defined by macropores of matrix 26. In another form however, the openings of matrix 26 may be defined by channels or passages that extend partially into or through the matrix. Still, in another form matrix 26 includes an engineered or structured geometry in the form of a framework that defines the openings. In other non-illustrated forms however, filler material 40 substantially fills only a portion of the openings of matrix 26. In the illustrated form, body 12 includes exposed portions of matrix 26 and filler material 40 all around and along its outer profile and external surface 14. More particularly, external surface 14, including the portions extending around the outer profile and following the shape of device 10 (including hollow interior 22), includes the exposed areas of matrix 26 and filler material 40. Additionally, while not illustrated in FIG. 1, body 12 also includes a plurality of openings positioned all around and along its outer profile and external surface 14, further details of which will be provided below in connection with FIG. 5. The openings are generally positioned within various locations of the exposed areas of matrix 26 and communicate with hollow interiors of struts of matrix 26. Still, in other forms the struts of matrix 26 can be provided without hollow interiors and include a solid or filled cross section. Similarly, in this form external surface 14 does not include any openings extending therethrough. In other forms however, it is contemplated that the struts of matrix 26 could be hollow while external surface 14 does not include any openings extending therethrough, or that external surface 14 could only be provided with openings in one or more desired regions. In other non-illustrated forms, it is contemplated that only a portion or distinct portions of external surface 14 may be provided with the exposed areas of matrix 26 and filler material 40. For example, in one such form, external surface 14 may only be provided with the exposed areas of matrix 26 and filler material 40 along top and bottom portions 18, 20. In another example, external surface 14 may only be provided with the exposed areas of matrix 26 and filler material 40 along the portion of sidewall 16 positioned proximate to chamber 22. Still, as would be appreciated by those skilled in the art, alternative configurations for the positioning of the exposed areas of matrix 26 and filler material 40 along external surface 14 are contemplated.

Figure 2:
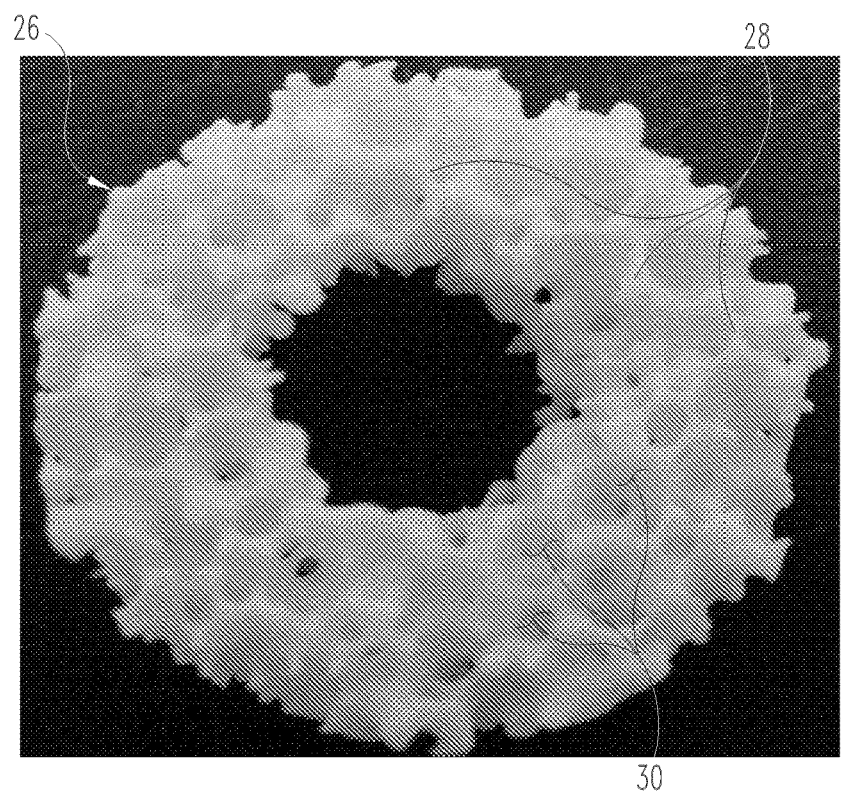
FIG. 2 depicts a photographic image of a porous matrix included in the implantable medical device of FIG. 1.
Figure 3:
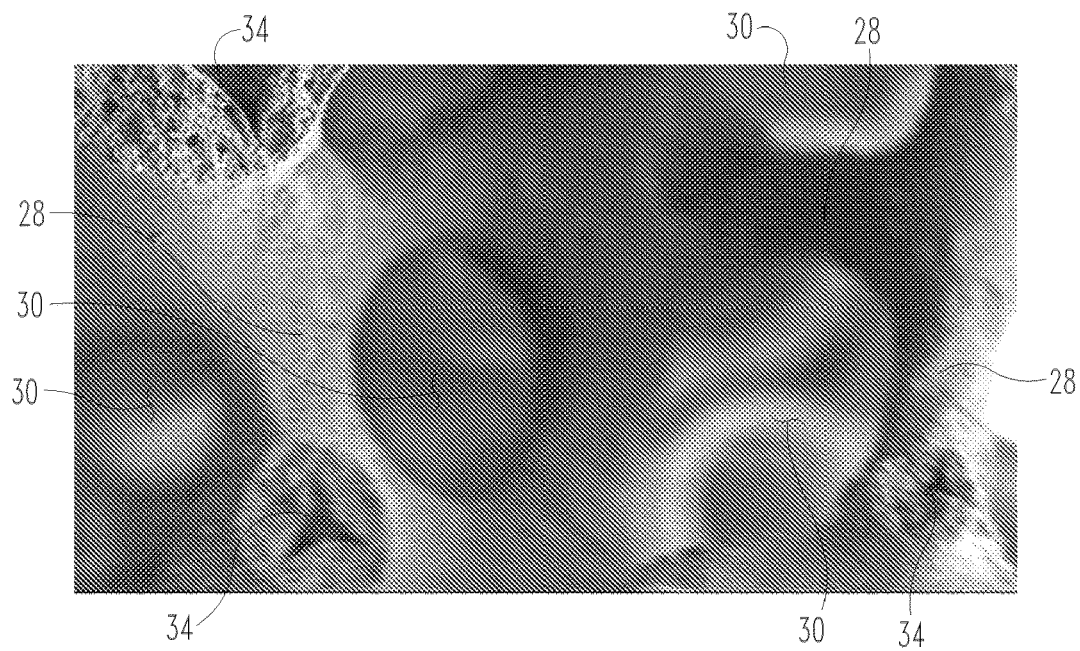
FIGS. 3 and 4 depict magnified photographic images of the porous matrix illustrated in FIG. 2.
Figure 4:
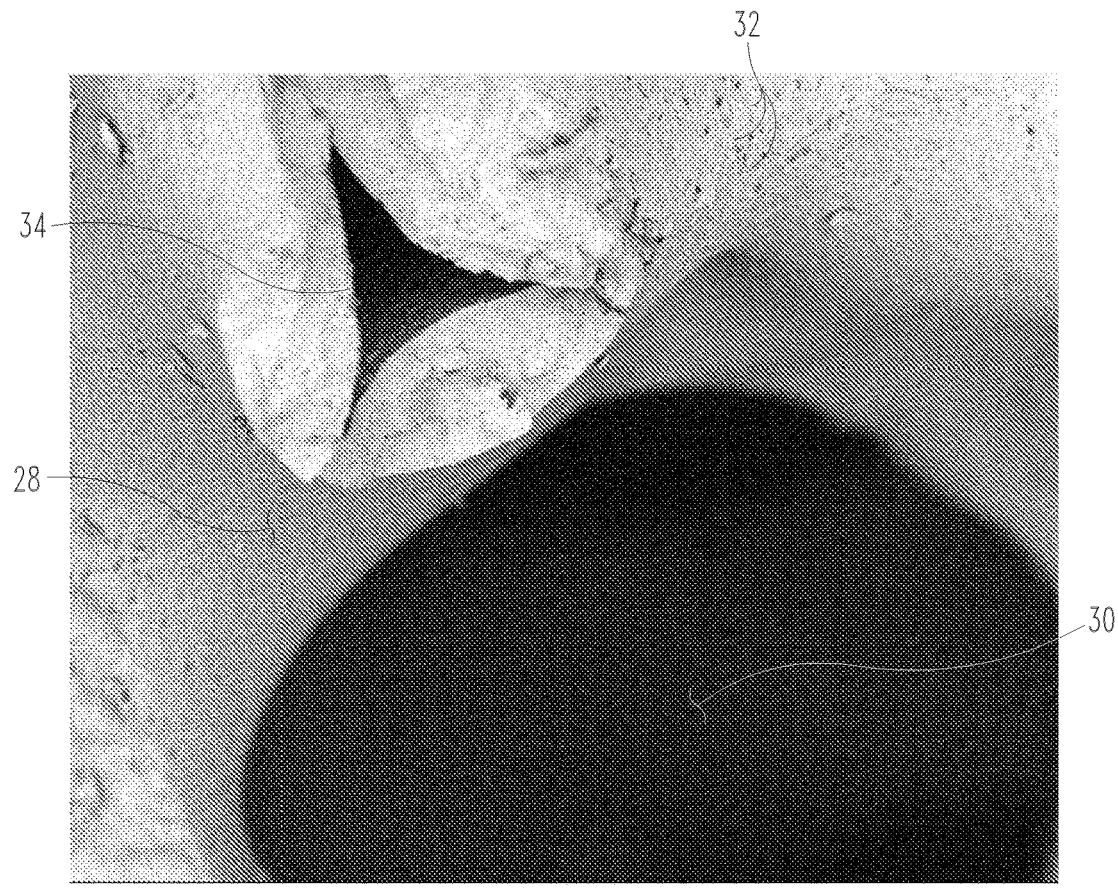

In FIG. 2 there is provided a photographic image of matrix 26 which provides a scaffold into which filler material 40 may be infused, although filler material 40 is absent from matrix 26 in FIG. 2. Matrix 26 includes a plurality of struts 28 that define a series of interconnected voids or macropores 30. Only a portion of struts 28 and macropores 30 have been labeled in FIG. 2 to preserve clarity. In the form illustrated in FIG. 2, matrix 26 generally has a hollow cylindrical shape, although it is contemplated that other configurations of matrix 26 may be utilized for device 10. Struts 28 of matrix 26 each include a hollow interior or passage 34 which can be seen in the magnified photographic images of matrix 26 in FIGS. 3 and 4. The passages 34 of struts 28 are interconnected in fluid communication with one another, thereby forming a hollow matrix of passages 34 that extends through struts 28. Similarly, passages 34 are generally isolated from the series of macropores 30 by the sidewalls of struts 28, although it is contemplated that some communication between passages 34 and macropores 30 may occur through micropores 32 (FIG. 4) on struts 28. A portion of passages 34 are exposed in FIGS. 3 and 4 for illustrative and clarity purposes, although it should be appreciated that passages 34 will generally not be exposed upon initial manufacturing of matrix 26 because the ends of struts 28 are generally closed, as will be appreciated in view of the process described below for making matrix 26. Rather, upon further processing, a portion of material at the end of struts 28 may be removed to expose passages 34. In this manner, one or more portions of matrix 26 can be impregnated with filler material 40 without passages 34 being filled with filler material 40. Similarly, when one or more portions of matrix 26 are impregnated with filler material 40, passages 34 remain substantially free of filler material 40 except for any unintended leakage that may occur through micropores 32, an end of a strut 28 that is not completely closed, or any other unintended surface cracks or defects. In the case of device 10, in one form passages 34 can be exposed following infiltration of one or more portions of matrix 26 with filler material 40 and upon shaping device 10 to its final configuration, further details of which are provided below.

In other forms, matrix 26 can be provided with struts 28 that do not include hollow interiors. Rather, in these forms, struts 28 are formed by the material from which matrix 26 is formed and include substantially solid cross-sectional configurations. Similarly, when one or more portions of matrix 26 are infiltrated and filled with filler material 40, it generally does not enter into or fill any portion of struts 28. Moreover, as suggested above, matrix 26 can also be formed to include one or more channels or passages that extend partially into or through the body and define openings of matrix 26 in lieu of macropores 30. Additionally, in another form matrix 26 includes an engineered or structured geometry in the form of a framework that defines openings of matrix 26.

Matrix 26 can be formed from a sintered or unsintered composite ceramic material that is synthetic, natural, bioresorbable or non-resorbable. In one aspect of this form, the ceramic material, which is radiopaque, provides device 10 with desirable imaging properties even after one or more portions of matrix 26 are filled with filler material 40. In one particular form, matrix 26 is formed from a sintered ceramic material that is osteoconductive and/or osteoinductive and is bioresorbable or biodegradable in vivo. Stated alternatively, the ceramic material is a bioactive material in that it may elicit a biological response at its surface which results in bond formation with adjacent tissue. Non-limiting examples of the ceramic material include calcium-based ceramics, such as calcium sulfate, calcium carbonate or a calcium phosphate material such as hydroxyapatite, carbonated apatite, fluroapatite, a tricalcium phosphate such as α-tricalcium phosphate or β-tricalcium phosphate, tetracalcium phosphate, octacalcium phosphate and mixtures thereof. In one particular form, matrix 26 may be formed from a bioresorbable or biodegradable ceramic material that undergoes a remodeling process having aspects that are substantially similar to certain aspects of the natural bone remodeling process. Thus, in contrast to other ceramic materials that exhibit non-specific dissolution that undermines the structural performance of initial bony attachment, the ceramic material of this form utilizes cell-based remodeling to provide an evolving yet stable host interface that maintains local structural performance throughout the bone replacement process. For example, in this form the ceramic material is progressively removed by osteoclast activity, where the micro-architecture of the removed portions of the ceramic material is progressively and sympathetically replaced by new bone formed through osteoblast activity. More particularly, the surfaces of the matrix facilitate an interfacial bond from the activity of bone cells that create an extracellular matrix that becomes solid through subsequent mineralization. One particular form of ceramic material that undergoes a remodeling process having aspects that are substantially similar to certain aspects of the natural bone remodeling process is Skelite®, which is an isolated bioresorbable biomaterial commercially available from Medtronic, Inc., 710 Medtronic Parkway, Minneapolis, Minn. 55432-5604 USA. More particularly, Skelite® is a compound that includes calcium, oxygen and phosphorous, wherein a portion of at least one of these elements is substituted with an element having an ionic radius of approximately 0.1 to 0.6 Å. Non-limiting examples of these elements include Silicon and Boron, although the use of other elements meeting the foregoing criteria is contemplated. Specifically, this biomaterial compound has the formula:

$$(Ca)_i\{(P_{1-x-y-z}B_xC_yD_z)O_j\}_2$$

wherein B, C and D are selected from those elements having an ionic radius of approximately 0.1 to 0.4 Å;
x is greater than or equal to zero but less than 1;
y is greater than or equal to zero but less than 1;
z is greater than or equal to zero but less than 1;
x+y+z is greater than zero but less than 1;
i is greater than or equal to 2 but less than or equal to 4; and
j is equal 4-δ, where δ is greater than or equal to zero but less than or equal to 1. Further details regarding this compound may be found in U.S. Pat. No. 6,323,146, the contents of which are incorporated herein by reference in their entirety.

For the illustrated form of matrix 26, it may be formed from an organic reticulated foam structure having a plurality of interconnected voids. More particularly, in one form, a polyurethane foam is flash-flamed to rupture and remove the thin walls between gas bubbles in the webs of the foam to provide a sponge where the pores are interconnected rather than closed. Porous foam structures having this configuration are commercially available or can be prepared, if desired, and facilitate the formation of passages 34 of struts 28. For those forms in which struts 28 are not hollow, matrix 26 can be formed using a pore forming agent such as polymeric spheres that are in contact at the time of matrix infusion with the ceramic material and then removed during sintering of the matrix. The foam structure is impregnated with an aqueous slurry of the ceramic material such that the ligaments or struts of the foam are coated and the voids are substantially filled. The excess slurry is removed from the pores and the coated structure is dried forming what is typically called a green body (i.e., an unsintered coated foam structure). Drying may take from a few minutes to over an hour as would be appreciated by those of skill in the art. This process is repeated until the coating of slurry attains the desired thickness throughout the foam structure. Typical thickness of coating may be about 10 to about 100 microns. The coated structure is then heated to first burn out the flexible organic foam and then sintered, thereby providing a fused ceramic foam having a plurality of interconnected voids in the form of macropores 30. Heating is typically done at temperatures of about 25° C. up to about 500° C. Sintering is typically conducted at temperatures of about 900° C. to about 1500° C. The heating and sintering may be done in succession such that the temperature is ramped up to the sintering temperatures from the heating temperatures.

Preparation of the slurry of ceramic material involves combining the ceramic material with a fluid medium, typically water, and a dispersing agent. Dispersing agents may be used to prevent agglomeration of the ceramic particles and can be either organic or inorganic. Examples of organic dispersants include sodium polyacrylate, ammonium polyacrylate, sodium citrate, sodium tartrate and mixtures thereof. Examples of inorganic dispersants include sodium carbonate, sodium silicate, tetrasodium pyrophosphate and mixtures thereof. The quantity of dispersing agent added is typically but not limited to between about 1 and 3.5 percent by volume.

It has been discovered that the initial particle size of the ceramic material can influence the strength of the final matrix 26. In addition, particle size can also influence both the solid loading capability and the resulting viscosity of the slurry. Milling a portion of the slurry has been found to be useful in obtaining the desired particle size distribution. Typically, a portion of the slurry may be milled between 1 and 24 hrs using an inert, abrasive-resistant milling media such as alumina or zirconia to provide ceramic particles of about up to 50 microns (and any size or ranges in size up to about 50 microns). In order for the ceramic particles of the slurry to adhere to both the foam substrate and to each other, it is desirable that, after particle size reduction, the slurry is thixotropic in nature. That is, viscosity of the slurry is reduced under increasing rates of shear.

Additives may also be added to the slurry of ceramic material before it is impregnated into the reticulated foam body. Non-limiting examples of such additives include a binder to impart strength to the green body, a wetting agent to improve distribution of the slurry throughout the foam, and an antifoaming agent that reduces the formation of bubbles in the slurry. These components are typically added to the slurry in small amounts, including but not limited to less than about 10 percent by volume for the binder and less than about 2 percent by volume for the wetting and antifoaming agents.

Matrix 26 can be provided with a compressive strength of about 10 MPa by applying several coats of the slurry of ceramic material and drying the impregnated structure between each coating. While the porous structure of the foam may begin to become clogged as the latter coats are applied, it has been found that using a slurry with a high solids loading (up to about 30 percent by volume) for the first several coats, followed by several coats with a slurry possessing a lower solids loading (below about 20 percent by volume) helps to avoid any clogging.

In one form, a vacuum process can be used to remove the excess slurry from the foam body. In this case, the impregnated foam is placed onto a mesh screen fitted to the top of a vertically mounted vacuum hose and the excess slurry is drawn through the hose into the vacuum unit. Alternately, a controlled gas jet can be used to disperse excess slurry that occludes internal pores.

To remove the foam structure, the dried, coated structure may be transferred to an electric furnace and heated to and held at a temperature sufficiently high (i.e. up to about 200° C.) to initially remove water and then at higher temperatures (e.g., up to about 500° C.) to pyrolyze the underlying polymer foam. Subsequent sintering of the ceramic structure (at temperatures of up to about 1500° C., more preferably about 1200° C. to about 1500° C.) is performed by heating to a temperature significantly higher than the temperature used to pyrolyze the foam. The furnace is then allowed to cool to room temperature.

While not previously described, it should be appreciated that one or more properties of the foam structure can be modified in order to provide matrix 26 with structural features that are desirable for one or more forms of device 10. For example, in one form, the foam structure can be provided with varying void fractions which can be used to provide matrix 26 in a form that will ultimately result in a matrix to filler material ratio that is targeted for certain strength and modulus characteristics. In one aspect of this form for example, it is contemplated that the dimensions of the macropores of the foam structure can be modified which will correspondingly modify the positioning of struts 28 of matrix 26. In another form, it is contemplated that the foam structure could be provided with an anisotropic configuration that will ultimately impart anisotropic properties to matrix 26. Similarly, device 10 could be formed with matrix 26 having anisotropic properties such that device 10 is provided with anisotropic properties that provide desired mechanical performance in one or more selected directions, similar to natural bone. In one aspect of this form, the anisotropic properties can be obtained with a foam structure that includes gradient porosity or elongated macropores. For example, the foam structure can be heated, stretched or compressed to elongate the macropores, and then cooled with the macropores retained in their elongated configuration. In another example, gradient porosity can be obtained by fusing together two or more foam structures that have macropores of differing sizes, although other alternative approaches are also contemplated.

It is also contemplated that the foam structure could be modified in a manner that results in one or more regions of device 10 being formed by a single material that is surrounded by matrix 26 and filler material 40. For example, portions of the foam structure may be removed from one or more regions and then these regions may subsequently be provided with the ceramic material, filler material 40 or another alternative material. In one particular form, a region formed of a single material may be utilized in an area of device 10 which is threadingly engaged by a placement device during implantation of device 10, although other uses of the one or more regions formed of a single material are contemplated. In addition to the foregoing, it is also contemplated that the foam structure could be formed by a three-dimensional printing process to include an organized or non-random arrangement of ligaments or struts. In this form, the foam structure can be provided in a ligament-based open cell network where the ligaments can be arranged to provide a configuration that will impart desired mechanical properties to matrix 26, and ultimately device 10.

In preparation of the illustrated form of device 10, filler material 40 is infused into and throughout the series of macropores 30 once matrix 26 has been prepared. However, as indicated above, in alternative forms filler material 40 is only infused into and used to fill a portion of the macropores 30 of matrix 26. In this configuration, one or more portions of device 10 can be provided with exposed areas of matrix 26 that are free from filler material 40, thereby providing increased exposure of matrix 26 and an open network into which tissue may grow. Filler material 40 generally reinforces the matrix 26 so device 10 can withstand loads and stresses commonly encountered at various skeletal locations and have mechanical properties than more closely emulate natural bone than what is achieved by matrix 26 alone. For example, filler material 40 may provide device 10 with high fracture toughness and a modulus of elasticity similar to bone. In one form, filler material 40 is a biologically stable polymeric material, although other types of biologically stable materials are contemplated. Non-limiting examples of biologically stable polymeric materials include polyethylene, polymethylmethacrylate, polyurethane, polysulfone, polyetherimide, polyimide, ultra-high molecular weight polyethylene (UHMWPE), cross-linked UHMWPE and members of the polyaryletherketone (PAEK) family, including polyetheretherketone (PEEK), carbon-reinforced PEEK, and polyetherketoneketone (PEKK). In another form, it is contemplated that filler material 40 may be a bioresorbable or biodegradable polymeric material, although other types of bioresorbable or biodegradable materials are contemplated. In one aspect of this form, filler material 40 may be provided in a form that includes a rate of degradation in vivo that is the same as or slower than the rate of degradation of matrix 26 when it is formed from a bioresorbable or biodegradable material. Non-limiting examples of bioresorbable or biodegradable polymeric materials include poly(L-lactide), poly (D,L-lactide), poly(L-co-D,L-lactide), polyglycolide, poly (lactide-co-glycolide), poly(hydroxylbutyrate), poly (hydroxyvalerate), tyrosine-derived polycarbonate, polyanhydride, polyorthoester, polyphosphazene, poly(dioxanone), poly(ε-caprolactone), and polyglyconate.

In one or more forms, filler material 40 may be provided as a composite material formed by, for example, a polymeric material and one or more osteoinductive and/or osteoconductive materials. For example, in one particular form, filler material 40 may be formed by a mixture of polymeric material and particles of the ceramic material from which matrix 26 is formed, although it is contemplated that alternative forms of ceramic or osteoinductive and/or osteoconductive materials could be utilized. In this arrangement, filler material 40 can be provided with additional exposed areas of osteoinductive and/or osteoconductive materials in order to promote additional bone bonding and/or increase the bioavailability of mineral elements eluted from device 10. Additionally, in one or more forms it is also contemplated that cells in contact with the particles of osteoinductive and/or osteoconductive materials in filler material 40 can be stimulated to help initiate the bone repair process.

It is contemplated that filler material 40 may be impregnated into and fill all or part of macropores 30 of matrix 26 in any suitable manner. In one particular form however, macropores 30 may be filled with filler material 40 by an injection molding process. For example, matrix 26 can be positioned within an appropriately sized mold into which filler material 40 can be injected under pressure. In one aspect of this form, the mold can be provided with an internal chamber that is larger than matrix 26 such that matrix 26 becomes enshrouded within filler material 40. As discussed above, in the illustrated form of matrix 26 where struts 28 are hollow, passages 34 of struts 28 remain substantially free of filler material 40 following the injection molding since each of the passages 34 is closed at the terminal portions of the corresponding strut 28 and generally isolated from the series of interconnected macropores 30. Moreover, in the form discussed above where one or more portions of device 10 can be provided with exposed areas of matrix 26 that are free from filler material 40, it is contemplated that corresponding areas of matrix 26 can be filled with a removable material, such as polyethylene glycol, waxes, hydrogels, or acrylic latexes, before filler material 40 is added to the remaining portion(s) of matrix 26. Similarly, once filler material 40 has been added to the desired areas of matrix 26, the removable material can be removed through dissolution with one or more solvents and/or by thermal treating, just to provide a few possibilities. In addition, while not previously described it should be appreciated that one or both of matrix 26 and filler material 40 can be treated to promote or improve interfacial chemical bonding therebetween. For example, in one form, it is contemplated that one or more polar functional groups, such as an ether or an ester, can be added to filler material 40. In another form, it is contemplated that matrix 26 may first be washed with ammonium hydroxide or some other solution that can alter polarity at its surfaces. Still, in another form it is contemplated that a surfactant or an emulsifying agent could be added to filler material 40. For example, in one aspect of this form it is contemplated that oleic acid could be added to filler material 40 before it is infused into one or more portions of matrix 26.

Following the injection molding process, matrix 26 and filler material 40 provide a composite blank that substantially corresponds in size and shape to the mold utilized during the injection molding process and can be further processed to provide device 10 in a desired configuration. For example, it is contemplated that the composite blank can be processed into the desired configuration of device 10 by any one or more of machining, cutting, laser shaping, chemical degradation, etching, grinding, and peening, just to provide a few non-limiting examples.

As the blank is processed into the final configuration of device 10, areas of matrix 26 become exposed at external surface 14 in addition to areas of filler material 40. In the illustrated form where struts 28 of matrix 26 included passages 34, the terminal portions and/or additional portions of at least a portion of struts 28 are removed during this processing, thereby providing openings 36 exposing corresponding passages 34 as illustrated in the photographic image of FIG. 5, which provides a magnified view of a representative example of a portion of external surface 14 of device 10. More particularly, strut 28 has been exposed to provide an exposed area of matrix 26 that surrounds opening 36 such that it is generally isolated from filler material 40. Accordingly, opening 36 provides an access point for bone and/or tissue to grow into passage 34 of the corresponding strut 28. Moreover, since each of the passages 34 is interconnected, it should be appreciated that bone and/or tissue growth into one passage 34 can spread into additional passages 34 even if such additional passages 34 are not exposed by an opening 36 at external surface 14. It should further be appreciated that, dependent on the amount of material removed from a terminal portion of a strut 28, exposed areas of matrix 26 could be provided that do not include any opening 36 that exposes the corresponding passage 34. In addition, openings 36, and to some extent the exposed areas of matrix 26, may generally be limited to those areas of device 10 that are subjected to additional processing following the injection molding process to achieve the desired configuration of device 10 from the composite blank formed by matrix 26 and filler material 40. Similarly, it is contemplated that in one form external surface 14 of device 10 could include numerous openings 36 and/or exposed areas of matrix 26, while in another form external surface 14 may only include a few openings 36 and/or exposed areas of matrix 26 dependent on the extent of the post-injection molding processing utilized. Still, in other forms where struts 28 are not hollow and do not include passages 34, openings 36 will be absent from external surface 14. Moreover, it is also contemplated that the areas of the blank which are processed following the injection molding process may be at least partially determined or influenced by considerations given to the anatomical location at which device 10 will be implanted.

In one or more forms, it is also contemplated that device 10 could be utilized to deliver a pharmacological agent. For example, in one form where matrix 26 is formed of a bioresorbable material, the pharmacological agent could be provided on the external surface of matrix 26 before macropores 30 are filled with filler material 40. In this form, the pharmacological agent could gradually become exposed in vivo as the matrix 26 is resorbed. In another form however, it is contemplated that the pharmacological agent could be provided in passages 34, although other variations for providing the pharmacological agent are envisioned. For example, in one alternative form it is contemplated that a pharmaceutical agent could be mixed into filler material 40 before it is infused into at least a portion of macropores 30 of matrix 26 and then delivered in vivo from filler material 40 following implantation of device 10. In one aspect of this form, filler material 40 may be provided as a biodegradable or bioresorbable material, such as a biodegradable or bioresorbable polymeric material, and the therapeutic agent can be progressively released from filler material 40 as it degrades or is resorbed.

As another alternative form, it is contemplated that a pharmaceutical agent could be provided on the exposed areas of filler material 40 after it has been infused into at least a portion of macropores 30 of matrix 26, and then delivered in vivo following implantation of device 10 from the exposed surfaces of filler material 40. In one aspect of this form, a pore forming agent can be used in filler material 40 as it is infused into at least a portion of macropores 30 of matrix 26 in order to provide one or more pores in filler material 40 into which the pharmaceutical agent can be deposited. In other aspects, it should be appreciated that the exposed areas of filler material 40 may subjected to chemical or mechanical processing before the pharmaceutical agent is provided thereon to enhance binding or adhesion between the pharmaceutical agent and filler material 40. Additionally or alternatively, the pharmaceutical agent may be subjected to chemical processing to enhance binding or adhesion between it and filler material 40. Still, in other aspects of this form it is contemplated that one or more types of bioresorbable adhesives may be used to attach the pharmaceutical agent to the exposed areas of filler material 40.

When included, the pharmacological agent may include a growth factor that may increase the rate of fusion, or may have some other beneficial effect. A wide variety of growth factors are contemplated for delivery by device 10. For example, the growth factor may include a bone morphogenetic protein, LIM mineralization proteins (LMPs), transforming growth factors, such as transforming growth factor-β(BGF-β) insulin-like growth factors, platelet-derived growth factors, fibroblast growth factors, or other similar growth factor that has some beneficial effect. If included, the growth factors, or other pharmacological agents, are typically provided in therapeutically effective amounts. For example, the growth factors may be included in amounts effective in promoting fusion.

In one particular form, the growth factor is a bone morphogenic protein, including recombinant human bone morphogenic proteins (rhBMPs). For example, in one form the bone morphogenetic protein is rhBMP-2, rhBMP-4 or heterodimers thereof. However, any bone morphogenetic protein is contemplated, including bone morphogenetic proteins designated as BMP-1 through BMP-18. Bone morphogenic proteins are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In other forms, the pharmacological agent may be one that is used for treating various spinal conditions, including infected spinal cords, cancerous spinal cords and osteoporosis. Such agents include antibiotics, analgesics and anti-inflammatory drugs, including steroids, although other exemplary agents are known to those skilled in the art. These agents are also used in therapeutically effective amounts that will treat the various conditions and the symptoms they cause and can be determined by the skilled artisan depending on the specific case.

In another non-illustrated embodiment, an implant includes exposed areas of an osteoconductive or osteoinductive material and a biologically stable material on its external surfaces where the osteoconductive or osteoinductive is suspended in or dispersed throughout the biologically stable material. More particularly, in one form of this embodiment, particles of a bioactive ceramic material, such as Skelite®, can be homogenously mixed with a biologically stable material, such as a biostable polymeric material including for example members of the polyaryletherketone (PAEK) family such as polyetheretherketone (PEEK), carbon-reinforced PEEK, and polyetherketoneketone (PEKK). The homogenous mixture may then be injection molded, extruded or compression molded into the desired configuration of the implant or a blank from which the desired configuration of the implant may be obtained through additional processing such as any one or a combination of machining, cutting, chemical degradation, etching, grinding, and peening, just to provide a few non-limiting examples. The exposed areas of the osteoconductive or osteoinductive material may generally promote accelerated fusion rates and provide early implant fixation through bony attachment while the biologically stable material continues to provide the mechanical properties necessary for the anatomical location at which the implant is utilized.

In another embodiment, an implantable medical device includes a body having an external surface defining an outer profile of the device. The external surface includes one or more exposed areas of a porous matrix exhibiting a series of interconnected macropores and a biologically stable filler material substantially filling at least a portion of the series of interconnected macropores. Following implantation, the porous matrix undergoes a remodeling process in which osteoclast activity progressively removes portions of the porous matrix and osteoblast activity progressively replaces the removed portions of the porous matrix with new bone tissue. In one or more aspects of this embodiment, initiation of the remodeling process is limited to the one or more exposed areas of the porous matrix on the external surface of the device. In another aspect of this embodiment, the porous matrix is formed by Skelite® and the biologically stable material is selected from polyetheretherketone (PEEK), carbon-reinforced PEEK, and polyetherketoneketone (PEKK).

In yet another embodiment, an implant includes a ceramic matrix having openings that are, in whole or in part, filled with a biologically stable filler material. The implant also includes an external surface extending around its outer profile. In one form of this embodiment, the external surface around the entire outer profile of the device is defined by exposed areas of the matrix and the biologically stable filler material. Stated alternatively, the external surface is defined by a discontinuous arrangement of interspersed areas of the matrix and the biologically stable filler material. In another form of this embodiment, the ceramic matrix is formed by Skelite® and the biologically stable material is selected from polyetheretherketone (PEEK), carbon-reinforced PEEK, and polyetherketoneketone (PEKK), although alternative materials for the ceramic matrix and filler material are contemplated.

In another embodiment, methods of stabilizing and promoting fusion between adjacent bones or bony portions along a load-bearing axis are provided. For example, in one form of this embodiment a method includes providing an implant, preferably a load bearing implant such as device 10 described above, and preparing adjacent vertebrae to receive the implant in an intervertebral disc space between the adjacent vertebrae. Such preparation methods are well known to those skilled in the art, and may include removing all or a portion of the intervertebral disc, including all or a portion of the annulus fibrosis or the nucleus pulposus. The implant may then be positioned in the intervertebral disc space between the adjacent vertebrae after the preparation step.

EXAMPLES

The following examples are for illustration purposes and are not to be construed as limiting the invention disclosed in this document to only the embodiments disclosed in these examples.

Example 1

A composite blank including a porous matrix formed of a bioresorbable ceramic material and a biologically stable polymeric material from which an implant, such as device 10, may be obtained was prepared in accordance with the following.

A cylindrical, open pore polyurethane foam having a diameter of 25 mm and a length of 25 mm was used as the precursor reticulated template. Two aqueous ceramic slurries were provided utilizing Skelite® commercially available from Medtronic, Inc., 710 Medtronic Parkway, Minneapolis, Minn. 55432-5604, USA. One slurry had a 25 vol % solids loading and the other a 17 vol % solids loading. Both slurries had been ball milled for 5 hrs. The foam material was immersed into the 25 vol % solids slurry and agitated to remove air to substantially fill the voids with the slurry, and to coat the struts of the foam with the slurry. The resultant impregnated foam was removed from the slurry and placed onto a mesh screen that was attached to a vertically mounted vacuum hose. Excess slurry was removed from the voids by turning on the vacuum unit for 3-5 seconds. This was sufficient time to remove excess slurry from the voids of the foam without disrupting the slurry that was adhered to the struts of the foam. The coated foam was oven dried at 120° C. for 15 minutes. This entire process was repeated 1-2 more times with the 25 vol % solids slurry and 4-10 more times with the 17 vol % solids slurry.

The dried, coated foam substrate was transferred to an electric furnace where it was heated at a rate of 1° C./min to a temperature of 500° C. to drive off water and to allow the polyurethane foam to pyrolyze without collapsing the porous ceramic matrix. The foam was held at 500° C. for 4 hrs and was subsequently heated at a rate of 1° C./min to a temperature of 1500° C. This temperature was held for 2 hours to permit the ceramic particles to sinter together thereby providing an open cell, porous ceramic matrix possessing the physical morphology of the original polyurethane foam material. Subsequently, the furnace was cooled at a rate of about 36° C./min until a final temperature of 25° C. was achieved. The final dimensions of the porous ceramic matrix were about 20 mm in diameter and about 20 mm in length and the density was approximately 2.9 g/cm3.

A PEEK injection molding machine was configured with an injection cavity sized to accommodate the porous ceramic matrix. The gating of the mold cavity was selected to ensure homogeneous and uniform filling of the cavity with the porous ceramic matrix in place. The mold temperature was set at approximately 120-200° C. and the barrel temperature was set at approximately 350-380° C. PEEK pellets were then loaded into the hopper of the injection molding machine from where it is fed on demand by an augur through a heater and into the mold cavity via a sprue. The PEEK material used was Victrex® PEEK 150G, a high performance unreinforced semi crystalline thermoplastic commercially available from Victrex USA, Inc., 300 Conshohocken State Road, Suite 120, West Conshohocken, Pa. 19428.

The porous ceramic matrix was loaded into the mold cavity when the injection molding machine was configured with the mold in the open position. The porous ceramic matrix was either directly loaded into the mold cavity or the scaffold was pre-heated to a temperature of about 230° C. prior to placement in the mold, as pre-heat reduces PEEK cool down upon contact with the porous ceramic matrix. The porous ceramic matrix geometry is such that the exterior profile substantially fills the mold cavity. The mold of the injection molding machine is then closed, thereby fully containing the porous ceramic matrix within the mold cavity.

In order to impregnate the open spaces of the porous ceramic matrix with the PEEK material, the PEEK is flowed into the mold cavity at an injection pressure of 1100 psi over a fill time of about seven minutes. Infiltration of the PEEK throughout the porous ceramic matrix during injection is assisted by maintaining a high mold temperature to reduce the viscosity of the PEEK during injection (attained utilizing a hot oil Thermolator from Budzar Industries, 38241 Willoughby Parkway, Willoughby, Ohio, 44094); using a central sprue which directs the PEEK down the center of the porous ceramic matrix; if the porous ceramic matrix has a hollow core, using a flow director within the hollow core to direct the flow of PEEK in a radial pattern to homogeneously fill the porous ceramic matrix; and preheating the porous ceramic matrix prior to insertion into the cavity to avoid localized cooling of the PEEK as it encounters the relatively cool porous ceramic matrix, thus maintaining reduced viscosity of the PEEK during injection.

The injection molding tool automatically ejects the porous ceramic matrix/PEEK composite blank from the cavity upon opening by the use of standard injection molding ejector pins. The composite blank is ejected to a collection chamber located underneath the tool for retrieval by the operator and can subsequently be machined to shape using implant machining practices which avoid chemical contamination by coolants, among other possibilities.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as falling within the scope of the invention, that scope being defined by the claims that follow. In reading the claims, it is intended that when words such as "a," "an," "at least one," "at least a portion" are used, there is no intention to limit the claim to only one item unless specifically stated to the contrary. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method for producing a medical implant, comprising:
   providing a bioresorbable ceramic matrix including a series of interconnected macropores defined by a plurality of interconnected struts, said interconnected struts each including a hollow interior;
   impregnating said ceramic matrix with a biologically stable polymeric material such that at least a portion of said series of interconnected macropores is substantially filled with said polymeric material and said hollow interiors remain hollow to provide a composite blank, said polymeric material comprising a material selected from the group consisting of polyetheretherketone (PEEK), carbon-reinforced PEEK, and polyetherketoneketone (PEKK); and
   processing said composite blank to provide an implant body including an external surface defining an outer profile of a configuration and shape for implantation, said implant body including a plurality of openings extending through at least a portion of said external surface and communicating with said hollow interior of at least a portion of said plurality of interconnected struts.

2. The method of claim 1, wherein said external surface further includes an exposed area of said polymeric material and an exposed area of said ceramic matrix.

3. The method of claim 1, wherein said hollow interiors are substantially free of said polymeric material.

4. The method of claim 1, wherein said impregnating includes injection molding said polymeric material into and around said ceramic matrix.

5. The method of claim 1, wherein said processing includes at least one of machining, cutting, etching, laser shaping and chemical degradation.

6. The method of claim 1, wherein said implant body has a compressive strength of about 10 MPa.

7. The method of claim 1, wherein:
   said ceramic matrix comprises a calcium based ceramic material defined by a compound that includes elements of calcium, oxygen and phosphorous, wherein a portion of at least one of said elements is substituted with an element having an ionic radius of about 0.1 to about 0.6 Å; and
   said ceramic matrix has a compressive strength of about 10 MPa.

8. The method of claim 1, wherein said ceramic matrix comprises Skelite® and has a compressive strength of about 10 MPa.

9. The method of claim 1, wherein said ceramic matrix is porous.

10. The method of claim 1, wherein said ceramic matrix is formed of at least one of an osteoconductive material and an osteoinductive material configured to be capable of undergoing a bone remodeling process.

* * * * *